United States Patent
Li

(10) Patent No.: US 9,248,057 B2
(45) Date of Patent: Feb. 2, 2016

(54) METHOD OF APPLYING BULK GLUE FOR NURSING PAD BASE FILM TO FOUR CORNERS OF SANITARY PRODUCT NURSING PAD BASE FILM AND DEVICE THEREFOR

(75) Inventor: Qiuhong Li, Beijing (CN)

(73) Assignee: Beijing Beishute Maternity & Child Articles., LTD, Beijing (CN)

( * ) Notice: Subject to any disclaimer, the term of this patent is extended or adjusted under 35 U.S.C. 154(b) by 0 days.

(21) Appl. No.: 14/349,399

(22) PCT Filed: Aug. 16, 2012

(86) PCT No.: PCT/CN2012/080209
§ 371 (c)(1),
(2), (4) Date: Apr. 3, 2014

(87) PCT Pub. No.: WO2014/026348
PCT Pub. Date: Feb. 20, 2014

(65) Prior Publication Data
US 2015/0164701 A1    Jun. 18, 2015

(51) Int. Cl.
| | |
|---|---|
| *B32B 37/12* | (2006.01) |
| *B32B 38/04* | (2006.01) |
| *A61F 13/15* | (2006.01) |
| *D21H 23/22* | (2006.01) |
| *D21H 27/00* | (2006.01) |
| *B32B 37/26* | (2006.01) |
| *B32B 37/00* | (2006.01) |
| *B32B 38/00* | (2006.01) |
| *B32B 38/18* | (2006.01) |

(52) U.S. Cl.
CPC ....... *A61F 13/15804* (2013.01); *B32B 37/0046* (2013.01); *B32B 37/1292* (2013.01); *B32B 37/26* (2013.01); *D21H 23/22* (2013.01); *D21H 27/001* (2013.01); *A61F 2013/1591* (2013.01); *B32B 37/0053* (2013.01); *B32B 38/0004* (2013.01); *B32B 38/1858* (2013.01); *B32B 2037/1215* (2013.01); *B32B 2037/268* (2013.01); *B32B 2555/00* (2013.01); *Y10T 156/1062* (2015.01); *Y10T 156/1077* (2015.01); *Y10T 156/1097* (2015.01); *Y10T 156/133* (2015.01)

(58) Field of Classification Search
CPC ............ Y10T 56/1077; Y10T 56/1097; Y10T 56/133; A61F 13/15; A61F 13/15577; A61F 13/15764; A61F 13/15772; A61F 13/15804; A61F 2013/15715; A61F 2013/15829; A61F 2013/15853; A61F 2013/1591; A61F 2013/15918; B32B 38/0004; B32B 2038/045; B32B 37/0053; B32B 2037/1215
See application file for complete search history.

(56) References Cited

U.S. PATENT DOCUMENTS

| | | | | |
|---|---|---|---|---|
| 4,762,582 A | * | 8/1988 | de Jonckheere | .. A61F 13/49019 156/164 |
| 5,235,515 A | * | 8/1993 | Ungpiyakul | ...... A61F 13/15699 156/264 |
| 6,129,810 A | * | 10/2000 | Schweitzer | ........... B65C 9/1803 156/387 |
| 2012/0055297 A1 | * | 3/2012 | Pedercini | ............... B26D 5/007 83/13 |
| 2012/0202664 A1 | * | 8/2012 | Brown | ............... A61F 13/15804 493/8 |

OTHER PUBLICATIONS

International Search Report, PCT/CN2012/080209, May 23, 2013.

* cited by examiner

*Primary Examiner* — Linda L Gray
(74) *Attorney, Agent, or Firm* — Synthesis Intellectual Property, LLC

(57) ABSTRACT

A method and a device for applying large areas of glue used for a bottom film of an absorbent pad at the four corners of the bottom film of the absorbent pad of a health care article is described. The processes includes (a) gluing and conveying a release paper; (b) cutting the glued release paper; and (c) transferring the glue from the release paper to the absorbent pad.

2 Claims, 3 Drawing Sheets

METHOD OF APPLYING BULK GLUE FOR NURSING PAD BASE FILM TO FOUR CORNERS OF SANITARY PRODUCT NURSING PAD BASE FILM AND DEVICE THEREFOR

CROSS-REFERENCE TO RELATED APPLICATIONS

This disclosure claims the benefit of priority to PCT/CN2012/080209 filed on Aug. 16, 2012, the disclosure of which is incorporated herein.

TECHNICAL FIELD OF THE INVENTION

The current invention relates to the technical field of a health care article of a bedding absorbent pad and, specifically, a method for applying large areas of glue used for a bottom film of a absorbent pad at the four corners of the bottom film of the absorbent pad of the health care article, and a device improved to realize the method.

TECHNICAL BACKGROUND OF THE INVENTION

When a consumer uses a bedding absorbent pad, as he turns over, stands up, lies and kicks, the absorbent pad will be moved, draped and folded, thus causing the bedding articles to be dirty. As to the traditional process, there is a method for applying glue at the four corners of a bottom film of the absorbent pad. This method may prevent a small size absorbent pad from being moved, draped and folded. As the glue piece applied at the four corners of the bottom film of the absorbent pad in the prior art has smaller size, the peeling force of the absorbent pad is smaller too. For example, a 50 mm×120 mm area of glue only has the peeling force of 1.0-1.5N. The bedding absorbent pad, under such a small peeling force, may not be firmly adhered to the bedding articles. Eventually, when the consumer turns over, stands up, lies and kicks, the absorbent pad will be moved, draped and folded, thus causing the bedding articles to be dirty.

In order to resolve the above mentioned issues, a feasible method is to increase the area of the glue at the four corners of the bottom film of the absorbent pad to improve the peeling force, which is a feasible method.

SUMMARY OF THE INVENTION

The technical issues that the current invention resolved is to provide a method for applying large areas of glue used for a bottom film of an absorbent pad at the four corners of the bottom film of the absorbent pad of a health care article, and a device improved to realize the method, preventing the incident that absorbent pad may be moved, draped and folded when in use while increasing the peeling force of a glue lump.

The invention adopts the following technical proposals to resolve the technical issues:

A method for applying a glue used for a bottom film of an absorbent pad at the four corners of the bottom film of the absorbent pad of a health care article comprises the following processes and steps:

(a) gluing and conveying a release paper: a pair of rubber rollers pull a release paper roll and synchronize the conveying speed of the release paper and the speed of a machine manufacturing the absorbent pad; the release paper roll is installed with an independent unwinding motor and controlled by a PLC and an inverter, so that the release paper roll may automatically decoil with the production speed of a machine, thus ensuring the release paper not to be pulled and fractured by the rubber roller; the release paper is intermittently glued by an automatically controlling glue gun during the transport process; the glue used for the bottom film of the absorbent pad is a hot melt glue, with a higher use temperature between 160° C.-180° C.; the glued release paper is conveyed to the next process by an adsorption conveying flat belt; the surface of the adsorption conveying flat belt has a long vent hole; a ring-shaped perforated flat belt is responsible for conveying the glued release paper and is externally connected with a negative pressure air pump, thus ensuring the glued release paper to be firmly absorbed on the surface of the belt and that the glued release paper, before being cut by a release paper knife, would not draped and deformed because of being heated; meanwhile, in order that the peeling force of a glue area used for the bottom film of the absorbent pad is ensured, the opening time of a hot melt glue shall be shortened as much as possible; compared with the narrower and shorter absorption conveying belt in the traditional process, under the premise that the opening time of the hot melt glue is ensured, the current absorption conveying belt is lengthened and widened, thus increasing the peeling force of the glue area used for the bottom film of the absorbent pad while ensuring the release paper not to be draped and deformed;

(b) cutting the release paper: a knife chisel and a knife roller are rotated to cut the glued release paper and the knife chisel conveys the cut release paper; the knife chisel is made of a high hardness material with a smooth surface, is matched with the knife roller and cuts the glued release paper; in order that the release paper knife does not cut the knife chisel at the same position each time and that the use time of the cutter is extended, the diameter of the knife chisel is longer that of the knife roller; suction holes are uniformly arranged on the surface of the knife chisel; an externally connected negative pressure air pump ensures the cut glued release paper to be transported on the surface of the knife chisel; a release paper knife is fixed on the knife roller of the release paper by a knife holder; the angle of the release paper knife is adjusted through the change of the angle of the knife holder of the release paper, thus solving the problem that the release paper knife cannot effectively cut the glued release paper; the release paper knife on the knife roller of the release paper is a straight knife as well as clamped and fixed by a pair of knife holders with 1° of angle; the knife holder comprises an upper knife holder (5.2.1) and a lower knife holder (5.2.2); and the reason for selecting an angled knife is to better cut the release paper under the conditions that a machine rotates in a high speed; and (c) transferring the glue used for the bottom film of the absorbent pad: the glue used for the bottom film of the cut absorbent pad, under the pressure of a compressing roller, is transferred to the bottom film of the absorbent pad; the compressing roller is preloaded with a force by a spring to some extent, is mounted on the surface of the absorbent pad, acts together with the knife chisel of the release paper and completes the adhesion between the glued release paper and the absorbent pad; and in order to obtain a better adhesion effect, the compressing roller is a rubber roller.

A device for achieving the method for applying large areas of glue used for the bottom film of the absorbent pad at the four corners of the bottom film of the absorbent pad of the health care article comprises:

a pair of rubber rollers used for pulling the release paper roll and synchronizing the conveying speed of the release paper and the speed of the machine manufacturing the absorbent pad;

an automatically unwinding motor used for independently unwinding the release paper roll, controlled by the PLC and the inverter, facilitating the release paper roll to automatically decoil with the production speed of the machine, and thus ensuring the release paper not to be pulled and fractured by the rubber roller;

an automatically controlling glue gun for intermittently gluing the release paper during the transport process;

an adsorption conveying flat belt used for conveying the glued release paper to the next process, wherein its surface has a long vent hole and it is externally connected with a negative pressure air pump;

a knife chisel and a knife roller used for rotating and cutting the glued release paper, wherein the knife chisel has a smooth surface and is made of high hardness material, is matched with the knife roller to cut the glued release paper; the knife roller has a smooth surface and is made of a stainless material; in order that the release paper knife does not cut the knife chisel at the same position each time, the use time of the release paper knife is extended, and the release paper is ensured to be cut, the diameter of the knife chisel is longer that of the knife roller; suction holes are uniformly arranged on the surface of the knife chisel, wherein the knife chisel is externally connected to a negative pressure air pump that ensures the cut glued release paper to be transported on the suction surface of the knife chisel; the novel process has encountered the following critical problem during real performance: as the width of the glued release paper is increased, the release paper is not easy to be cut by the release paper knife; however, using angled release paper knife may solve the problem; the release paper knife is fixed on the knife roller of the release paper by a knife holder; the angle of the release paper knife is adjusted through the change of the angle of the knife holder, thus completely solving the problem that the release paper knife may not effectively cut the glued release paper; the release paper knife on the knife roller of the release paper is a straight knife as well as clamped and fixed by a pair of knife holders with 1° of angle; the knife holder comprises an upper knife holder and a lower knife holder; and the reason for selecting an angled knife holder is to better cut the release paper under the conditions that the machine rotates in a high speed; and a compressing roller disposed on the knife chisel, wherein the glued release paper, under the combined action of the pressure of the knife chisel and the compressing roller, is transferred to the bottom film of the absorbent pad; the compressing roller is preloaded with a force by a spring and mounted on the surface of the knife chisel; the absorbent pad passes through the gap between the compressing roller and the knife chisel; when the glued release paper is rotated with the knife chisel and contacts the bottom film of the absorbent pad, the glue surface, which is not glued and under the action of preloaded force, is firmly adhered to the bottom film of the absorbent pad and completes the adhesion between the glued release paper and the bottom film of the absorbent pad; and the compressing roller is a silicone roller.

The current invention has the following positive effects: large areas of glue may be applied on the bottom film of the absorbent pad, thus ensuring the absorbent pad not to be moved, draped and folded when in use and increasing the peeling force of the glue area used for the bottom film of the absorbent pad. During actual production, taking the 160 mm*160 mm area glue as an example, the peeling force of the glue area may reach 20N or more than 20N; the width of the area glue applied on the bottom film of the absorbent pad may reach 60 mm-450 mm; the length of the area glue may reach 120 mm-1000 mm; the normal production speed of the machine of making the absorbent pad which the four corners are adhered with large areas of glue may reach 120-180 m/minute, resolving the issue that the absorbent pad would be moved, draped and folded when in use and meeting the market's requirements for industrialized production of the absorbent pad with large areas of glue. When the absorbent pad having large areas of glue is in use, it will not be moved, draped or folded when the consumer turns over, stands up, lies or kicks, thus preventing the bedding articles from getting dirty.

EMBODIMENTS OF THE INVENTION

Figure 1:
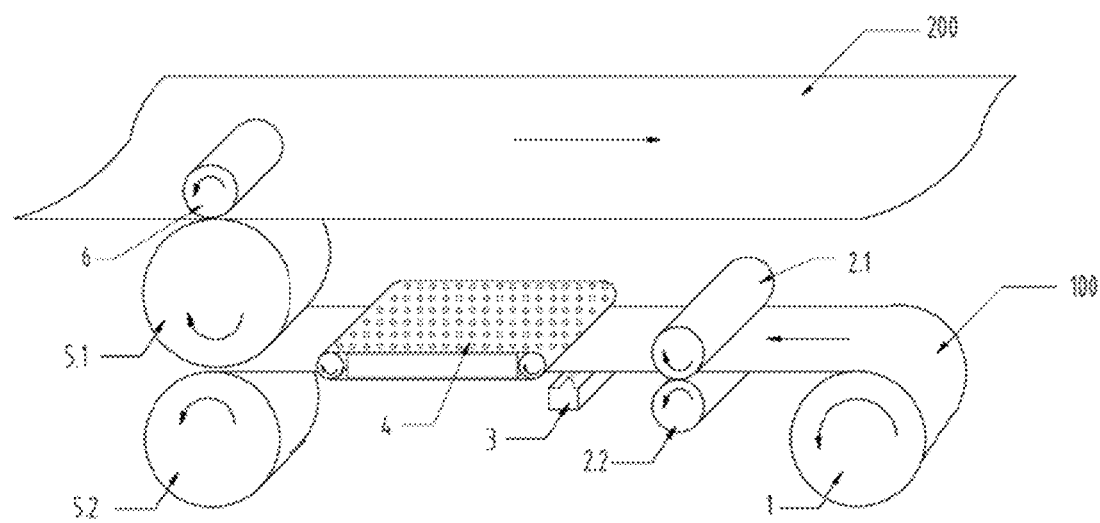
FIG. 1 is a brief structural diagram of the invention.
Figure 2:
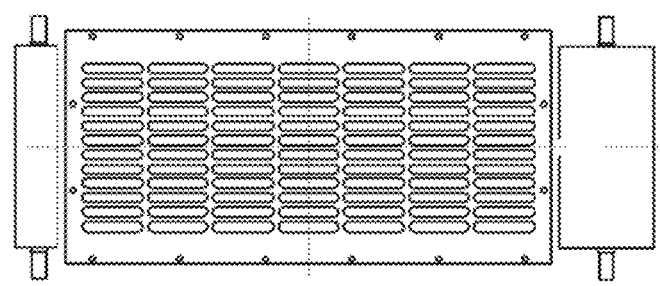
FIG. 2 is a structural diagram of a suction conveying flat belt of the invention.
Figure 3:
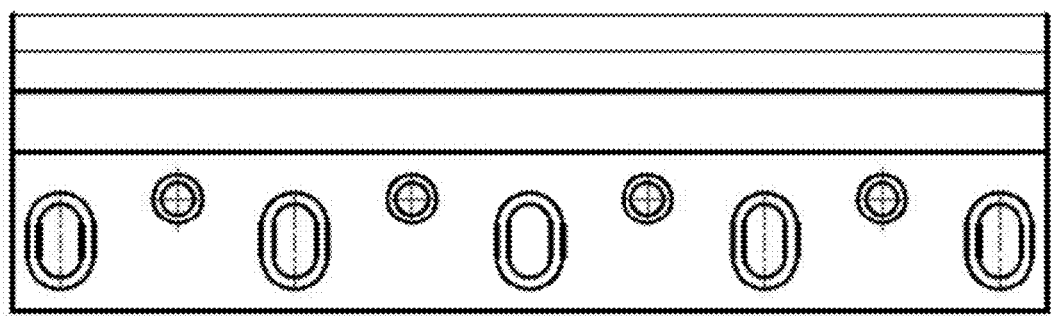
FIG. 3 is a diagram of a release paper knife clamped at a knife roller by an upper knife holder and a lower knife holder.
Figure 4:
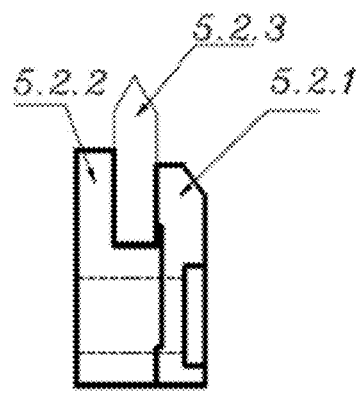
FIG. 4 is a lateral view corresponding to FIG. 3.
Figure 5:
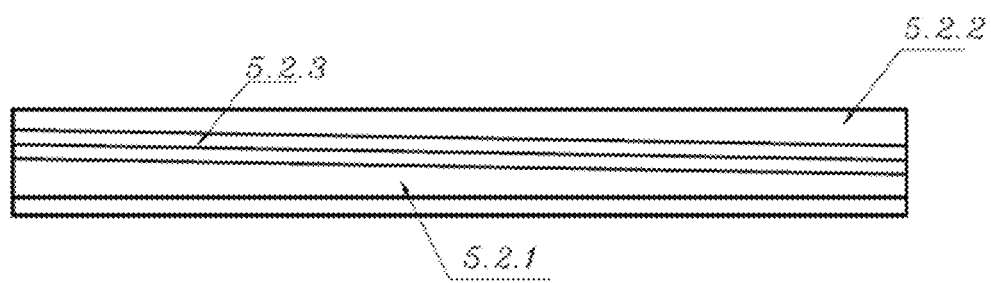
FIG. 5 is a top view corresponding to FIG. 3.

A method for applying large areas of glue used for a bottom film of an absorbent pad at the four corners of the bottom film of the absorbent pad of a health care article comprising the following processes and steps:

(a) gluing and conveying a release paper: a pair of rubber rollers 2.1, 2.2 pull a release paper roll 1 and synchronize the conveying speed of the release paper 100 and the speed of a machine manufacturing the absorbent pad 200; the release paper roll is mounted with an independent unwinding motor and controlled by a PLC and an inverter, so that the release paper roll may automatically decoil with the production speed of the machine, thus ensuring the release paper not to be pulled and fractured by the rubber roller; the release paper is intermittently glued by an automatically controlling glue gun 3 during the transport process; the glue used for the bottom film of the absorbent pad is a hot melt glue, with a higher use temperature between 160° C.-180° C.; the glued release paper is then conveyed to the next process by an adsorption conveying flat belt; the surface of the adsorption conveying flat belt has a long vent hole; and a ring-shaped perforated flat belt is responsible for conveying the glued release paper and is externally connected with a negative pressure air pump;

(b) cutting the release paper: a knife chisel 5.1 and a knife roller 5.2 are rotated to cut the glued release paper and convey the cut glued release paper; the knife chisel 5.1 has a smooth surface and is made of a high hardness material, and it is matched with the knife roller 5.2 to cut the glued release paper; in order that a release paper knife does not cut the knife chisel at the same position each time, and that the use time of the knife is extended, the diameter of the knife chisel is longer that of the knife roller; suction holes are uniformly arranged on the surface of the knife chisel, wherein it is externally connected to a negative pressure air pump that ensures the cut glued release paper to be transported on the surface of the knife chisel; the release paper knife is fixed on the knife roller of the release paper by a knife holder; the angle of the release paper knife is adjusted through the change of the angle of the knife holder; the release paper knife on the knife roller 5.2 of the release paper is a straight knife as well as clamped and fixed by a pair of knife holders with 1° of angle; the knife holder comprises an upper knife holder 5.2.1 and a lower knife holder 5.2.2; and (c) transferring glue piece used for the bottom film of the absorbent pad: the cut adhesive glue piece of the release paper, under the pressure of a compressing roller 6, is transferred to the bottom film of the absorbent pad; the compressing roller 6 is firstly preloaded with force by a spring to some extent and is mounted on the surface of the knife chisel; the absorbent pad passes through the gap between the compressing roller and the knife chisel; when the glued release paper is rotated with the knife chisel and contacts the bottom film of the absorbent pad, the glue surface, which is not glued and under the action of the preloaded force, is firmly adhered on the bottom film of the absorbent pad and completes the adhesion between the glued release paper and the bottom film of the absorbent pad; and in order to have a better adhesion effect, the compressing roller is a silicone roller.

A device for achieving the method for applying large areas of glue used for the bottom film of the absorbent pad at the four corners of the bottom film of the absorbent pad of the health care article comprises:

a pair of rubber rollers 2.1, 2.2 used for pulling a release paper roll 1 and synchronizing the conveying speed of the release paper 100 and the speed of a machine manufacturing the absorbent pad 200;

an automatically unwinding motor used for independently unwinding the release paper roll, controlled by the PLC and the inverter, facilitating the release paper roll to automatically decoil with the production speed of the machine, and thus ensuring the release paper not to be pulled and fractured by the rubber roller;

an automatically controlling glue gun 3 for intermittently gluing the release paper during the transport process;

an adsorption conveying flat belt 4 used for conveying the glued release paper to the next process, having a long vent hole on its surface and being externally connected with the negative pressure air pump;

a knife chisel 5.1 and a knife roller 5.2 used for rotating and cutting the glued release paper; wherein the knife chisel 5.1 has a smooth surface and is made of a high hardness material, wherein it is matched with the knife roller 5.2 to cut the glued release paper; the diameter of the knife chisel is longer than that of the knife roller; suction holes are uniformly arranged on the surface of the knife chisel; and it is externally connected to a negative pressure air pump that ensures the cut glued release paper to be transported on the suction surface of the knife chisel; The release paper knife 5.2.3 is fixed on the knife chisel 5.2 through the upper knife holder 5.2.1 and the lower knife holder 5.2.2; the angle of the release paper knife is adjusted through the change of the angle of the knife holder of the release paper; the release paper knife on the knife roller 5.2 of the release paper is a straight knife as well as clamped and fixed by a pair of the knife holders with 1° of angle; the knife holder comprises a upper knife holder 5.2.1 and a lower knife holder 5.2.2; and a compressing roller 6 disposed on the knife chisel 5.1, wherein the glue used for the bottom film of the absorbent pad, under the pressure of the compressing roller 6, is transferred to the bottom film of the absorbent pad; the compressing roller 6 is preloaded with force by a spring and mounted on the surface of the knife chisel; the absorbent pad passes through the gap between the compressing roller and the knife chisel; when the glued release paper is rotated with the knife chisel and contacts the bottom film of the absorbent pad, the glue surface, which is not glued and under the action of the preloaded force, is firmly adhered to the bottom film of the absorbent pad and completes the adhesion between the glued release paper and the bottom film of the absorbent pad; and the compressing roller is a silicone roller.

The invention is not limited to the above embodiments. Other products may be obtained by anyone under the teaching of the current invention. Regardless of any change in its forms and structures, the technical proposals, being the same with or similar to the invention, all are within the protection scope of the current invention.

The invention claimed is:

1. A method for applying large areas of glue to four corners of a bottom film of an absorbent pad of a health care article, the method comprising:
   (a) gluing and conveying a release paper:
      providing a pair of rubber rollers which pull a release paper from a release paper roll, synchronizing a conveying speed of the release paper and a speed of a machine manufacturing the absorbent pad; wherein the conveying speed of the release paper and the speed of the manufacturing machine are synchronized with an independent release paper unwinding motor controlled by a programmable logic controller (PLC) and an inverter;
      providing intermittent glue to the release paper by an automatically controlling glue gun; wherein the glue is a hot melt glue with a higher use temperature between 160° C.-180° C.; and then
      conveying the glued release paper by a conveying flat belt; wherein a surface of the conveying flat belt has a plurality of vent holes, and wherein the conveying flat belt is connected with a negative pressure air pump;
   (b) cutting the glued release paper:
      conveying the glued release paper to a knife chisel and a knife roller which are rotated and cut the glued release paper; wherein the knife chisel has a smooth surface which includes a high hardness material, wherein a diameter of the knife chisel is greater than that of the knife roller; wherein the knife chisel includes suction holes uniformly arranged on the surface, and wherein the suction holes are connected to a negative pressure air pump; the knife roller includes a release paper knife fixed thereon by a knife holder; an angle of the release paper knife is adjusted through the change of an angle of the knife holder; wherein the release paper knife is a straight knife and fixed between an upper knife holder and a lower knife holder with 1° of angle along the length of the knife holder; and
   (c) transferring the intermittent glue on the release paper:
      contacting the intermittent glue carried on the release paper and the bottom film of the absorbent pad; compressing the glue between the release paper and the bottom film with a compressing roller which is preloaded by a spring; wherein the absorbent pad passes through a gap between the compressing roller and the knife chisel; thereby firmly adhering the glue to the bottom film of the absorbent pad and completing the adhesion of the glued release paper and the bottom film of the absorbent pad; wherein the compressing roller is a silicone roller.

2. A device for applying large areas of glue to four corners of a bottom film of an absorbent pad, the device comprising:
   a pair of rubber rollers positioned to and adapted for pulling a release paper from a release paper roll and synchronizing a conveying speed of the release paper and a speed of a machine manufacturing an absorbent pad;
   an automatically unwinding motor controlled by a programmable logic controller (PLC) and the inverter, which facilitates the release paper roll to automatically uncoil with the production speed of the machine, and thus ensuring the release paper not to be pulled and fractured by the rubber roller;
   an automatically controlling glue gun for intermittently gluing the release paper during a transport process;

a conveying flat belt positioned between the pair of rubber rollers and a knife chisel and a knife roller, used for conveying the glued release paper to the next process, and having a plurality of vent holes on its surface;

a negative pressure air pump connected to the conveying flat belt;

a knife chisel and a knife roller used for rotating and cutting the glued release paper;

wherein the knife chisel includes a smooth surface comprised of a high hardness material;

wherein a diameter of the knife chisel is greater than that of the knife roller; wherein the knife chisel further includes suction holes uniformly arranged on the surface and connected to a negative pressure air pump; wherein the knife roller includes a release paper knife is fixed on the knife roller by a knife holder; wherein an angle of the release paper knife can be changed by changing an angle of the knife holder; wherein the release paper knife is a straight knife and clamped and fixed by an upper knife holder and a lower knife holder with 1° of angle along the length of the knife holder; and a compressing roller disposed on the knife chisel adapted to provide pressure to transfer the glue to the bottom film of the absorbent pad; wherein the compressing roller is preloaded with force by a spring and wherein the compressing roller is mounted on the surface of the knife chisel; and wherein the compressing roller is a silicone roller.

\* \* \* \* \*